US006987999B1

(12) United States Patent
Kroll

(10) Patent No.: US 6,987,999 B1
(45) Date of Patent: Jan. 17, 2006

(54) IMPLANTABLE DEFIBRILLATOR WITH ALTERNATING COUNTER ELECTRODE

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 588 days.

(21) Appl. No.: 10/138,457

(22) Filed: May 2, 2002

(51) Int. Cl.
*A61N 1/39* (2006.01)

(52) U.S. Cl. ............................................. 607/5
(58) Field of Classification Search ............... 607/4–5
See application file for complete search history.

(56) References Cited

U.S. PATENT DOCUMENTS

| | | | |
|---|---|---|---|
| 4,641,656 A | 2/1987 | Smits ..................... 128/419 D |
| 4,727,877 A * | 3/1988 | Kallok ......................... 607/5 |
| 4,932,407 A | 6/1990 | Williams ................ 128/419 D |
| 5,224,475 A | 7/1993 | Berg et al. .............. 128/419 D |
| 5,344,430 A | 9/1994 | Berg et al. ...................... 607/8 |
| 5,441,518 A * | 8/1995 | Adams et al. .................. 607/5 |
| 5,531,764 A | 7/1996 | Adams et al. .................. 607/5 |
| 5,601,607 A * | 2/1997 | Adams ........................... 607/5 |
| 5,690,686 A | 11/1997 | Min et al. ....................... 607/5 |
| 5,713,926 A | 2/1998 | Hauser et al. .................. 607/5 |
| 5,766,226 A | 6/1998 | Pedersen ........................ 607/5 |
| 5,916,238 A | 6/1999 | Hauser et al. .................. 607/5 |
| 5,978,704 A | 11/1999 | Ideker et al. ................... 607/5 |
| 5,978,705 A | 11/1999 | KenKnight et al. ............ 607/5 |
| 6,067,471 A | 5/2000 | Warren ........................... 607/5 |
| 6,076,014 A | 6/2000 | Alt ................................. 607/4 |
| 6,122,553 A | 9/2000 | Ideker et al. ................ 607/122 |
| 6,157,860 A | 12/2000 | Hauser et al. .................. 607/9 |
| 6,246,908 B1 | 6/2001 | Chattipakorn et al. ......... 607/5 |
| 6,251,125 B1 | 6/2001 | KenKnight et al. ............ 607/5 |
| 6,266,563 B1 | 7/2001 | KenKnight et al. ............ 607/5 |
| 6,275,730 B1 | 8/2001 | KenKnight et al. ............ 607/5 |
| 6,280,462 B1 | 8/2001 | Hauser et al. .................. 607/5 |
| 6,327,499 B1 | 12/2001 | Alt ................................. 607/4 |
| 6,449,506 B1 * | 9/2002 | Sh. Revishvili et al. ........ 607/5 |
| 6,658,289 B2 * | 12/2003 | Helland .......................... 607/4 |
| 6,735,472 B2 * | 5/2004 | Helland .......................... 607/5 |

OTHER PUBLICATIONS

Leonelli FM et al., Energy steering of biphasic waveforms using a transvenous three electrode system. Pacing Clin Electrophysiol. 1999;22:849-54.

Olovsky MR et al., The effect of shock configuration and delivered energy on defibrillation impedance. Pacing Clin Electrophysiol. 1999;22: 165-8.

Gold MR, et al., Effects of an active pectoral-pulse generator shell on defibrillation efficacy with a transvenous lead system. Am J Cardiol. 1996;78:540-3.

Sweeney RJ et al., Defibrillation efficacy using high-frequency switching to proportion current among simultaneous shock pathways. J Cardiovasc Electrophysiol 1997;8:271-80.

* cited by examiner

*Primary Examiner*—Robert E. Pezzuto
*Assistant Examiner*—Kristen Mullen

(57) ABSTRACT

An implantable cardiac stimulation device delivers successive defibrillation waveforms using alternating counter electrodes selected from a case electrode and an electrode located on a coronary sinus lead. The case electrode and coronary sinus electrode may be selected individually in an alternating fashion such that the defibrillation pathway alternates between two single pathways during a defibrillation regimen. The case electrode and the coronary sinus electrode may also be used simultaneously in parallel to create a dual pathway. Defibrillation waveforms may then be delivered in a cyclical fashion between the individual counter electrodes and the combined counter electrodes such that alternation between single pathways and a dual pathway is achieved.

25 Claims, 4 Drawing Sheets

IMPLANTABLE DEFIBRILLATOR WITH ALTERNATING COUNTER ELECTRODE

FIELD OF THE INVENTION

The present invention relates generally to implantable medical devices and more specifically to an implantable defibrillating device equipped with more than one counter electrode and an associated method for automatically alternating defibrillation waveform pathways during a defibrillation regimen.

BACKGROUND OF THE INVENTION

An implantable cardioverter-defibrillator, commonly referred to as an "ICD," is capable of recognizing tachycardia or fibrillation and delivering electrical therapy to terminate such arrhythmias. ICDs are often configured to perform pacemaking functions as well. A pacemaker generally delivers rhythmic electrical pulses to the heart to maintain a normal rhythm in patients having conduction abnormalities or bradycardia, which is too slow of heart rate. Pathologic tachycardia, which is a rapid heart rate not associated with a normal physiologic response such as a response to exercise, is typically treated with low to moderate-energy shocking pulses. The treatment of tachycardia is often referred to as "cardioversion." Fibrillation is characterized by rapid, unsynchronized depolarizations of the myocardial tissue. Ventricular fibrillation is most often fatal if not treated within a few minutes of its onset. The termination of fibrillation, referred to as "defibrillation," is accomplished by delivering high-energy shocking pulses.

Upon detection of fibrillation, a defibrillation therapy, referred to herein as a "regimen," delivered by an implantable defibrillator may include delivery of multiple defibrillation waveforms. Each waveform is defined by a number of parameters including the shape and energy of each pulse. A conventional wave shape is a biphasic waveform in which two pulses that have opposite polarity are generated on the order of 100 microseconds apart. Each waveform within a regimen is delivered on the order of 10 seconds apart. During the time between each defibrillation waveform, the capacitor used for delivering the next waveform is charged, and the defibrillator re-determines if fibrillation is still present. If fibrillation is no longer detected, the regimen is terminated prior to delivering another shock.

Early implantable defibrillation systems required a thoracotomy to allow placement of electrode patches on the epicardial surface of the heart. The risk of morbidity and mortality associated with an open thoracic approach led to the development of transvenous systems that are available today. Transvenous systems include placement of a lead in the right side of the heart with an electrode in the right ventricle, typically near the apex, and a second proximal electrode, typically in the superior vena cava. However, defibrillation using a single lead in the right side of the heart is not successful in all patients and implantation of an epicardial patch is commonly indicated.

The relatively large physical size of early implantable defibrillators, due to large capacitors needed for delivering the high-energy shocks, restricted the implantation of the device to the abdominal region. As capacitor technology has improved, the size of the defibrillators has decreased making pectoral implantation feasible. With the ability to implant the device in the pectoral region, the housing of the device becomes available as an active electrode, sometimes referred to as an "active can," in combination with the right ventricular lead eliminating the need for an epicardial patch electrode in most patients. Thus, the pectoral implantation of the device overcame the need for a thoracic approach.

Implantable defibrillation systems have been described that use either single or dual defibrillation pathways utilizing combinations of two or three electrodes, selected from a right ventricular lead and the active can. Investigations have been made to determine the optimal defibrillation electrode configuration and results show improved effectiveness of active can configurations, particularly with dual pathway defibrillation using three electrodes.

As the device size continues to be reduced, however, the effectiveness of active can configurations comes into question. Development of coronary sinus electrodes, implanted endovascularly in the area of the left heart, provides additional electrode configurations available for defibrillation. With new configurations available between electrodes implanted in the right ventricle and endovascular electrodes on the left side of the heart, investigation continues for determining the optimal electrode configuration for achieving successful defibrillation at the lowest energy requirement.

However, no single defibrillation electrode configuration will be optimal for all patients. Differences in implant location, patient anatomy and disease state, which can change overtime, will result in different optimal electrode configurations between patients and perhaps within the same patient over time. A given defibrillation pathway selected as the primary pathway based on clinical testing may not continue to be the optimal defibrillation pathway. Therefore, a final determination of an optimal electrode configuration remains elusive.

The use of multiple single or dual pathways during a defibrillation regimen, therefore, would be advantageous in patients who are not successfully treated by the first defibrillation shock waveform delivered along a primary pathway. An implantable defibrillation device is needed, therefore, which allows automatic switching between defibrillation pathways during a defibrillation regimen.

SUMMARY OF THE INVENTION

What is described herein is an implantable cardiac stimulation device equipped with a right ventricular lead, a coronary sinus lead, and a case electrode for delivering defibrillation therapy. The size of the device is such that it is suitable for implantation in the pectoral region. Thus, either the case electrode, provided by the device housing, or an electrode located on the coronary sinus lead, positioned in the vicinity of the left side of the heart, may function as the counter electrode during high voltage shock delivery for the purpose of defibrillation.

Each of the case electrode and the coronary sinus electrode provides a different defibrillation pathway through the heart tissue when paired with an electrode located on the right ventricular lead. The case electrode and a coronary sinus electrode may also be selected concurrently as parallel counter electrodes, creating a dual pathway from an electrode located on the right ventricular lead.

A method is provided for automatically alternating the counter electrode assignment between the single case electrode, the single coronary sinus electrode and the parallel combination of the case and coronary sinus electrodes during a defibrillation regimen. By alternating the defibrillation pathway, defibrillation success may be improved when the first waveform of a defibrillation regimen fails to terminate fibrillation.

When operating according to a preferred embodiment, a defibrillation waveform is first delivered upon detection of ventricular fibrillation by selecting an electrode located on a coronary sinus lead as the counter electrode paired with a right ventricular electrode. If the ventricular fibrillation is not terminated, a second defibrillation waveform is delivered by selecting the case electrode as the counter electrode paired with the right ventricular electrode. If the ventricular fibrillation is still not terminated, a third defibrillation waveform is delivered by selecting a coronary sinus electrode and the case electrode together as counter electrodes in parallel, creating a dual pathway for defibrillation.

A physician may determine the preferred counter electrode to be used as the primary pathway based on clinical testing. If fibrillation is not terminated after delivering a defibrillation waveform via this primary path, alternative single or dual pathways are selected by selecting a different single or combined counter electrode. The method provided herein, therefore, allows automatic cycling between a coronary sinus electrode and a case electrode as the counter electrode during a defibrillation regimen. The method further allows automatic cycling between a parallel combination of counter electrodes for a dual pathway and a single counter electrode for a single pathway.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DETAILED DESCRIPTION OF PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout. The present invention is directed at providing automatic cycling between defibrillation pathways during a defibrillation regimen. A general cardiac stimulation device will be described in conjunction with FIGS. 1 and 2, in which the features included in the present invention could be implemented. It is recognized, however, that numerous variations of such a device exist in which the methods included in the present invention could be implemented without deviating from the scope of the present invention.

Figure 1:
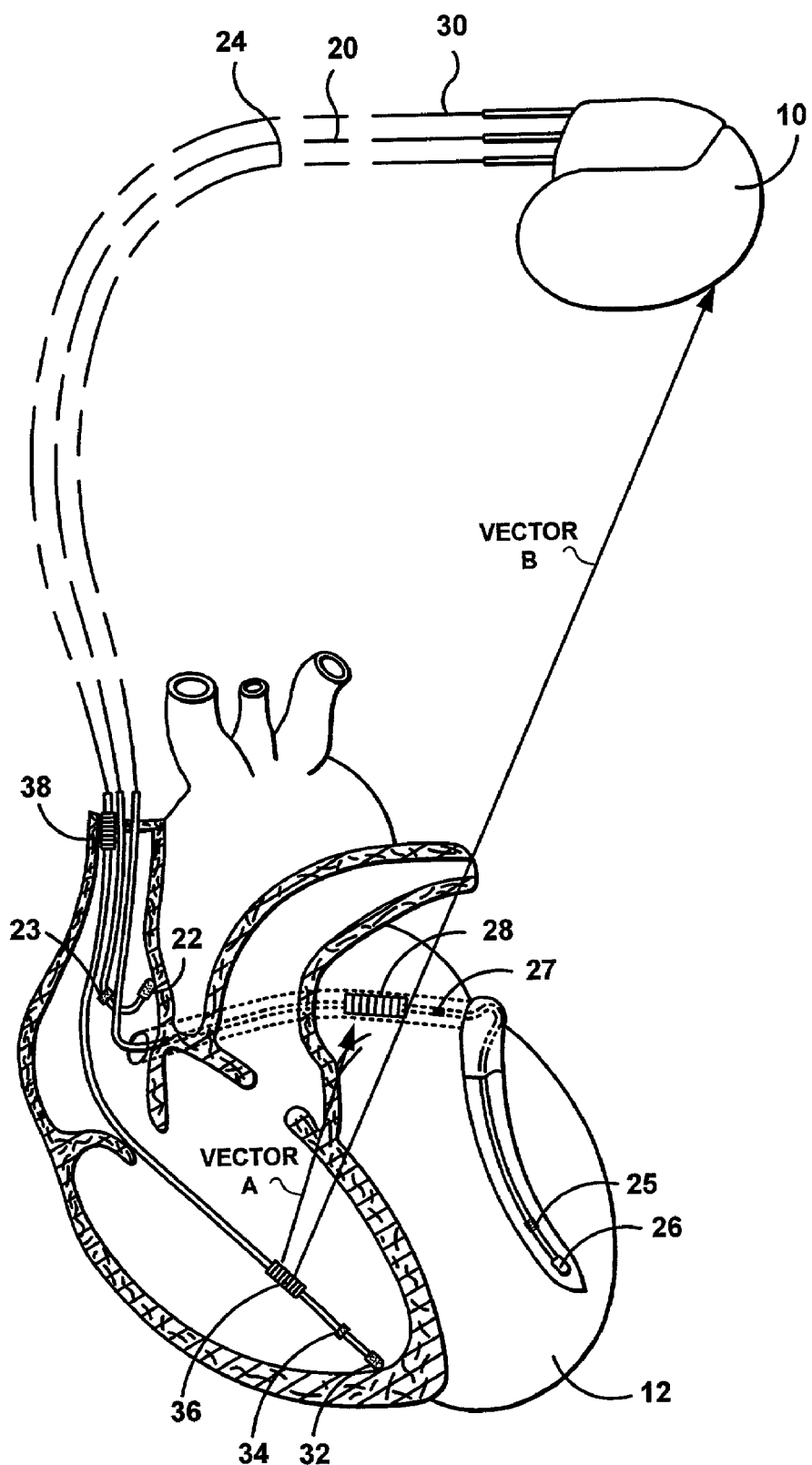
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to: receive atrial and ventricular cardiac signals; deliver left ventricular pacing therapy using at least a left ventricular tip electrode 26 for unipolar configurations or in combination with left ventricular ring electrode 25 for bipolar configurations; deliver left atrial pacing therapy using at least a left atrial ring electrode 27, and deliver shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
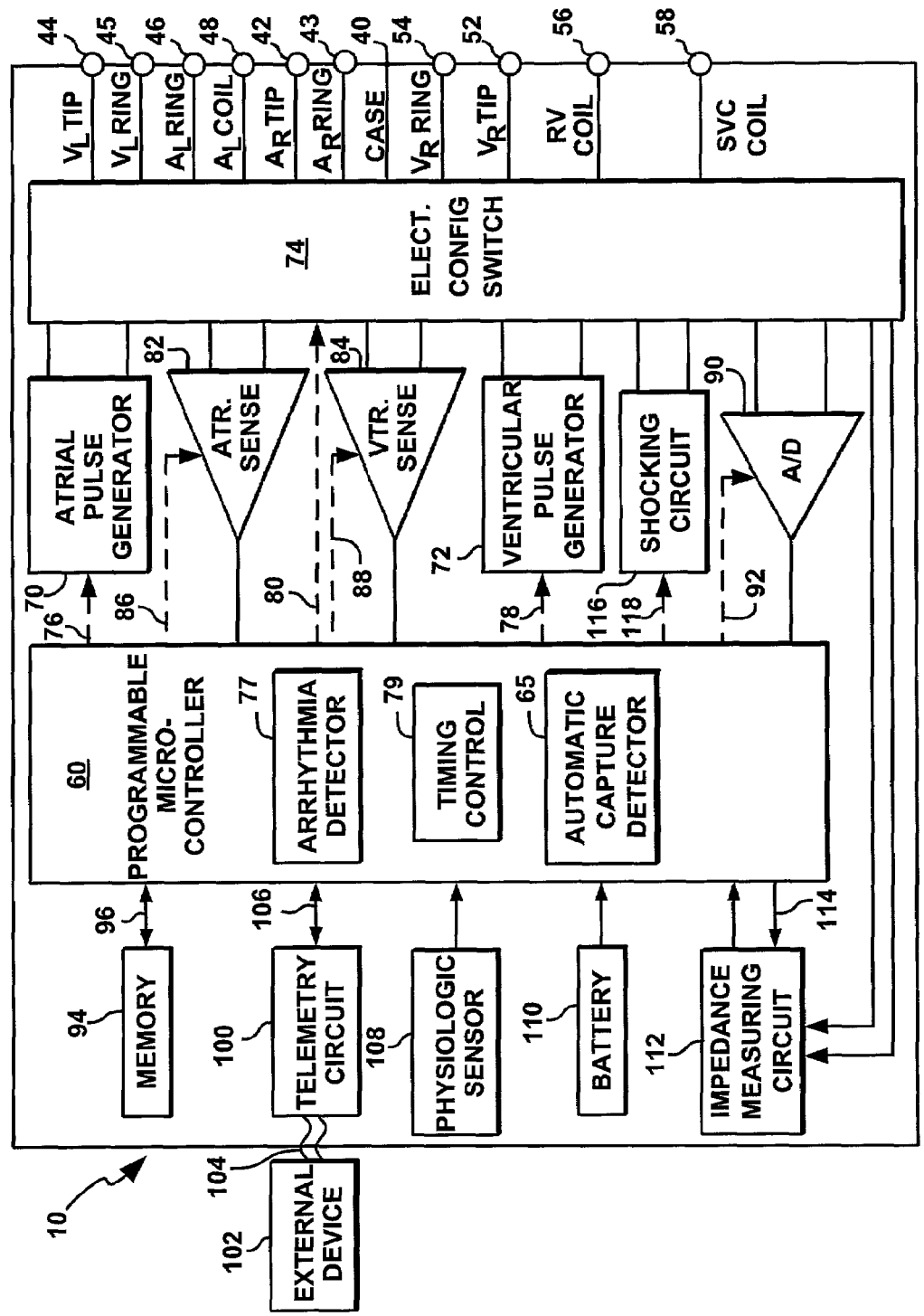
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can," "case," or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The housing 40 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the right atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interchamber (A—A) delay, or ventricular interchamber (V—V) delay, etc.), as well as to keep track of the timing of refractory periods, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g. unipolar, bipolar, cross-chamber, etc.) by selectively closing the appropriate combination of switches as is known in the art. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" refers to the process of noting an electrical signal. "Detection" refers to the step of confirming that the sensed electrical signal as the signal being sought by the detector. As an example, "detection" applies to the detection of both proper rhythms (i.e., "R wave" or "R wave") as well as improper dysrhythmias including arrhythmia and bradycardia (e.g., detection of the absence of a proper rhythm.)

The timing intervals between sensed events (e.g. P-waves, R-waves, and depolarization signals associated with fibrillation which are sometimes referred to as "F-waves" or "Fib-waves") are then classified by the arrhythmia detector 77 by comparing them to a predefined rate zone limit (e.g. bradycardia, normal, low rate ventricular tachycardia, high rate ventricular tachycardia, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (EGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 2, the microcontroller 60 includes an automatic capture detector 65 that searches for an evoked response signal following a stimulation pulse during a "detection window" set by timing control circuitry 79. The microcontroller 60 enables the data acquisition system 90 via control signal 92 to sample the cardiac signal that falls in the capture detection window. The sampled signal is evaluated by automatic capture detector 65 to determine if it is an evoked response signal based on its amplitude, peak slope, morphology or another signal feature or combination of features. The detection of an evoked response during the detection window indicates that capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source shown as a battery 110 that provides operating power to all the circuits shown in FIG. 2. For the stimulation device 10, which employs shocking therapy, the battery 110 must be capable of operating at low current drains for long periods of time, preferably less than 10 $\mu$A, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

Since stimulation device 10 is intended to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11 to 40 joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as a counter electrode (that provides a return electrical path) in combination with the RV electrode 36, or as part of a split electrical vector using the SVC coil electrode 38 or the left atrial coil electrode 28 creating a dual defibrillation pathway.

As illustrated in FIG. 1, one possible defibrillation pathway, represented by vector A, exists between the RV electrode 36 and the left atrial coil electrode 28. Another possible defibrillation pathway, represented by vector B, may exist between the RV electrode 36 and the housing 40. A dual defibrillation pathway represented by both vectors A and B exists when the left atrial coil electrode 28 and the housing 40 are selected, concurrently, to function as parallel counter electrodes. In accordance with the present invention, successive defibrillation waveforms may be delivered along these defibrillation pathways in an alternating fashion.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

A number of defibrillation waveforms may be delivered during a given defibrillation regimen in response to fibrillation detection. Preferably, the device 10 verifies that fibrillation is still present following the delivery of one waveform prior to delivering the next waveform. In accordance with the present invention, if one waveform delivered along one pathway fails to defibrillate the heart, the next waveform is delivered along an alternative pathway by selecting, through switch 74, an alternative counter electrode.

Figure 3:
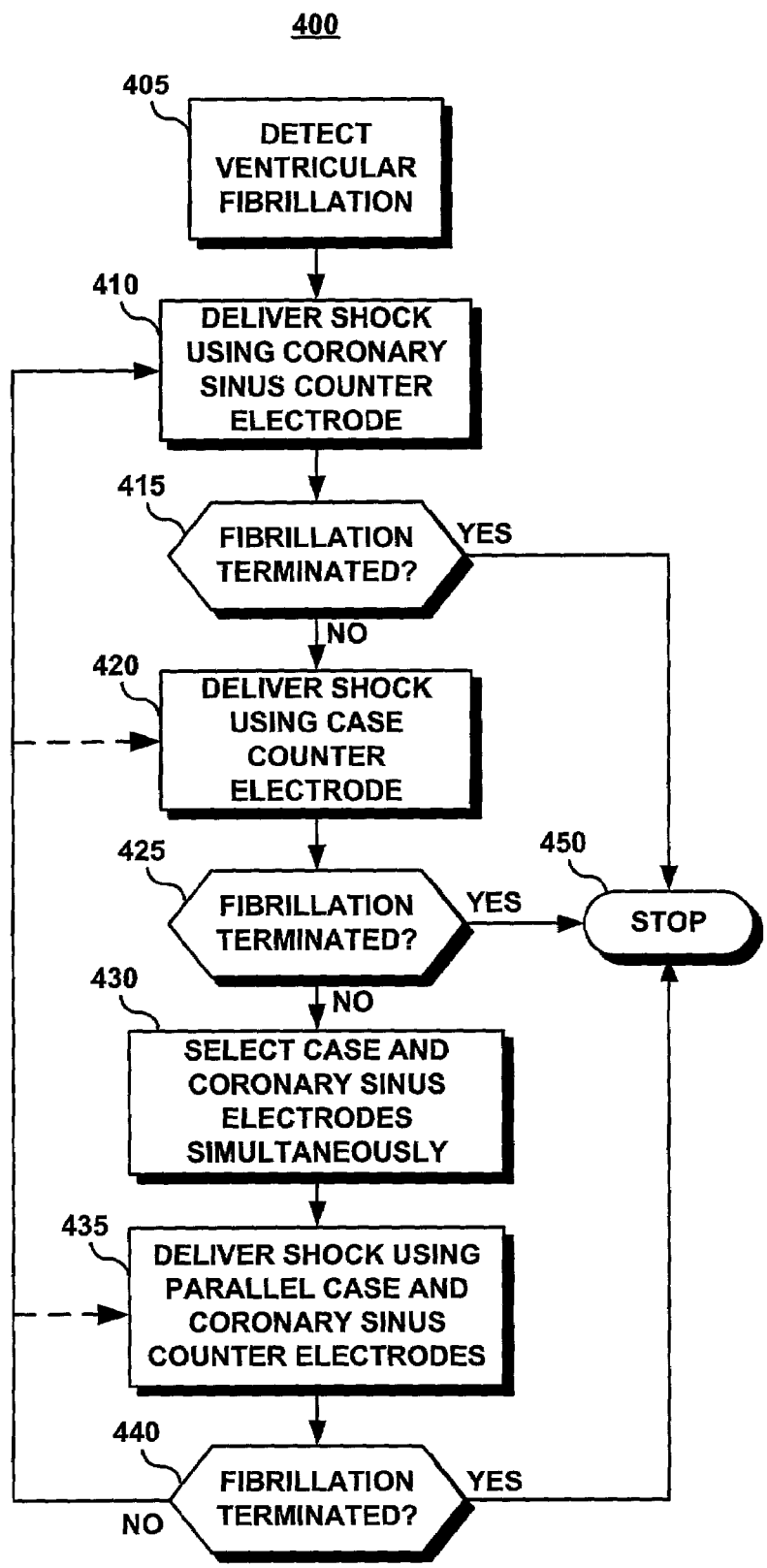
FIG. 3 is a process flow chart illustrating a method used by the implantable stimulation device of FIG. 2, for automatically cycling between counter electrodes on successive defibrillation waveforms during a defibrillation regimen.

FIG. 3 illustrates a method 400 implemented by the device 10, for automatically alternating the defibrillation pathway of successive waveforms during a defibrillation regimen. In this flow chart, the various algorithmic steps are summarized in individual "blocks". Such blocks describe specific actions or decisions that must be made or carried out as the algorithm proceeds. Where a microcontroller (or equivalent) is employed, the flow chart presented herein provides the basis for a "control program" that may be used by such a microcontroller (or equivalent) to effectuate the desired control of the stimulation device. Those skilled in the art may readily write such a control program based on the flow chart of FIG. 3 and other descriptions presented herein.

Method 400 is initiated at step 405 when ventricular fibrillation is detected by arrhythmia detector 77. A defibrillation waveform is delivered at step 410 between the right ventricular coil electrode 36 to the left atrial coil electrode 28, such that the defibrillation waveform follows a pathway represented by vector A shown in FIG. 1. At step 415, arrhythmia detector 77 determines if the ventricular fibrillation has been terminated. If fibrillation has been successfully terminated, method 400 is concluded at step 450.

If fibrillation is still detected at decision step 415, a second defibrillation waveform is delivered from the right ventricular coil electrode 56 to the housing 40 at step 420. The delivery of this waveform will follow the pathway illustrated by vector B shown in FIG. 1. At step 425, arrhythmia detector 77 determines if fibrillation has now been successfully terminated. If so, method 400 is concluded at step 450.

In one embodiment, method 400 may continue alternating between the left atrial coil electrode 28 as the counter electrode and the housing 40 as the counter electrode between successive waveforms, until defibrillation is confirmed or the maximum allowed number of waveforms to be delivered during the regimen has been reached.

In one embodiment, the first and second waveforms are the same type of waveform (e.g., a biphasic waveform). In an alternate embodiment, the first and second waveforms are different (e.g., a monophasic waveform and a biphasic waveform), where one type of waveform can be used for a certain electrode configuration, and the other waveform can be used for a different electrode configuration.

In the embodiment shown in FIG. 3, if fibrillation has still not been terminated at decision step 425, the switch 74 selects the housing 40 and the left atrial coil electrode 28, concurrently, to form a parallel counter electrode combination. A third defibrillation waveform is delivered at step 435 from the right ventricular coil 56 to the parallel counter electrodes forming a dual pathway illustrated by both vectors A and B shown in FIG. 1.

At step 440, arrhythmia detector 77 determines if the fibrillation is now terminated. If so, method 400 is concluded at step 450. If fibrillation continues to be detected, method 400 may return to any of steps 410, 420, or 435, as desired or programmed, to deliver another shock, as described above. Method 400 may continue to cycle between the following three defibrillation pathways, either in a linear, predetermined regimen, or alternatively, in another predetermined or programmed regimen: 1) the single pathway to the left atrial coil electrode 28, 2) the single pathway to the housing 40, and 3) the dual pathway to the concurrently selected left atrial coil electrode 28 and housing 40. The energy, shape, and maximum number of waveforms in each regimen may be predetermined according to device specifications or programmed as desired by a clinician.

The method 400 shown in FIG. 3 describes one algorithm for cycling between two single pathways and one dual pathway. The order by which the counter electrodes are selected for determining these pathways is preferably programmable. The primary counter electrode, that is the counter electrode used on the first defibrillation attempt, is preferably selected by a clinician based on clinical testing.

Depending on the implanted system, a number of single counter electrodes or parallel counter electrodes could be selected. The concept of the present invention for alternating waveform delivery between different single, dual or even multiple pathways may be used successfully in any implantable defibrillator system equipped with at least three or more electrodes suitable for delivering high voltage therapy. Both atrial and ventricular high-voltage therapy could be delivered using a method of alternating or cycling counter electrodes.

Figure 4:
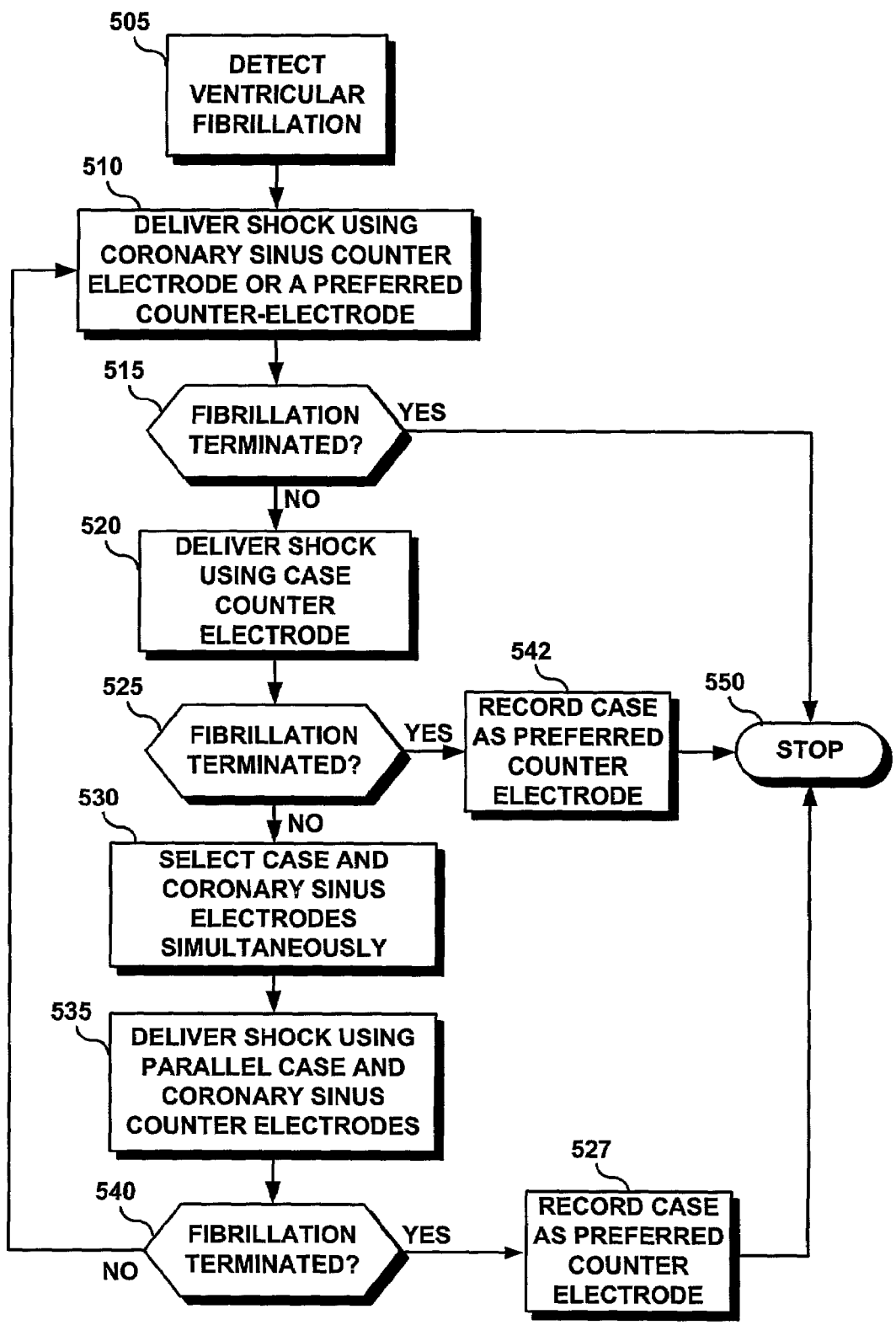
FIG. 4 is a process flow chart illustrating an alternative method used by the implantable stimulation device of FIG. 2, for automatically cycling between counter electrodes on successive defibrillation waveforms during a defibrillation regimen.

FIG. 4 illustrates another method 500 implemented by the device 10, for automatically alternating the defibrillation pathway of successive waveforms during a defibrillation regimen, by learning and following the best pathways (i.e., counter-electrodes). Method 500 is initiated at step 505 when ventricular fibrillation is detected by arrhythmia detector 77. A defibrillation waveform is delivered at step 510 between the right ventricular coil electrode 36 to the left atrial coil electrode 28, such that the defibrillation waveform follows a pathway represented by vector A shown in FIG. 1. Otherwise, if this pathway has proven not to be ineffective, then the defibrillation waveform is delivered using a previously stored preferred counter electrode.

At step 515, arrhythmia detector 77 determines if the ventricular fibrillation has been terminated. If fibrillation has been successfully terminated, method 500 is concluded at step 550. If fibrillation is still detected at decision step 515, a second defibrillation waveform is delivered from the right ventricular coil electrode 56 to the housing (or case electrode) 40 at step 520. The delivery of this waveform will follow the pathway illustrated by vector B shown in FIG. 1.

At step 525, arrhythmia detector 77 determines if fibrillation has now been successfully terminated. If so, method 500 proceeds to step 527 where it logs the housing 40 as the preferred counter electrode for future use at step 515, and is then concluded at step 550.

If fibrillation has still not been terminated at decision step 525, the switch 74 selects the housing 40 and the left atrial coil electrode 28, concurrently, to form a parallel counter electrode combination. A third defibrillation waveform is delivered at step 535 from the right ventricular coil 56 to the parallel counter electrodes forming a dual pathway illustrated by both vectors A and B shown in FIG. 1.

At step 540, arrhythmia detector 77 determines if the fibrillation is now terminated. If so, method 500 proceeds to step 542 where it records the dual counter electrode configuration as the preferred counter electrode for future use at step 515, and is then concluded at step 550.

As an optional addition to method 500, whenever a maximum energy shock fails with a given counter electrode, then that counter electrode is excluded from the next therapy regimen delivered. However, if all 3 counter electrodes fail the first time when used at maximum energy, then they are presumed to be functioning properly. All these 3 counter electrodes are relisted in an "approved" category, and process 400 of FIG. 3 is initiated. It is noteworthy to mention that the impedances will be different between the different counter electrodes. Thus, the device 10 will be able to deliver the optimal waveform timing for each counter electrode which may vary.

Thus a system and method have been described for cycling between alternative single and combined parallel counter electrodes when delivering successive defibrillation waveforms during a defibrillation regimen. While detailed descriptions of specific embodiments of the present invention have been provided, it would be apparent to those reasonably skilled in the art that numerous variations of the methods described herein are possible in which the concepts of the present invention may readily be applied. The descriptions provided herein are for the sake of illustration and are not intended to be exclusive.

What is claimed is:

1. A method of automatically alternating between at least a first counter electrode positioned adjacent a left cardiac chamber and a second remotely disposed counter electrode, for use in a cardiac defibrillator, comprising:

detecting a fibrillation;

delivering a first defibrillation waveform using a coil electrode positioned in a right chamber, and any of the first or second counter electrodes, so that the first defibrillation waveform follows a first pathway;

determining if fibrillation was successfully terminated;

if fibrillation was not successfully terminated, automatically delivering a second defibrillation waveform using the coil electrode and any of the first or second counter electrodes, so that the second defibrillation waveform follows a second pathway through the heart tissue, wherein the second pathway is different from the first pathway; and repeating an automatic alternating delivery of the first defibrillation waveform and the second defibrillation waveform until defibrillation is confirmed or the maximum allowed number of waveforms to be delivered has been reached.

2. The method of claim 1, wherein automatically and alternately delivering at least the first and second defibrillation waveforms comprises programmably delivering the first and second defibrillation waveforms in a programmable sequence.

3. The method of claim 1, wherein the maximum allowed number of waveforms to be delivered is at least four waveforms.

4. A method of defibrillating a heart using a right ventricular coil electrode, a coronary sinus counter electrode, and a case counter electrode, the method comprising:

detecting a fibrillation;

delivering a first defibrillation waveform using a first electrode configuration comprising the right ventricular coil electrode and at least one of the coronary sinus counter electrode and the case counter electrode;

determining if fibrillation was successfully terminated;

if fibrillation was not successfully terminated, automatically delivering a second defibrillation waveform using a second electrode configuration comprising the right ventricular coil electrode and at least one of the coronary sinus counter electrode and the case counter electrode, wherein the second electrode configuration is different from the first electrode configuration; and repeating an alternating delivery of the first defibrillation waveform and the second defibrillation waveform until defibrillation is confirmed or the maximum allowed number of waveforms to be delivered has been reached.

5. The method of claim 4, wherein delivering at least the first and second defibrillation waveforms comprises programmably delivering the first and second defibrillation waveforms in a programmable sequence.

6. The method of claim 4, wherein the maximum allowed number of waveforms to be delivered is at least four waveforms.

7. A method of automatically alternating between at least a first counter electrode positioned adjacent a left cardiac chamber and a second remotely disposed counter electrode, for use in a cardiac defibrillator, comprising:

detecting a fibrillation;

delivering a first defibrillation waveform using a coil electrode positioned in a right chamber, and any of the first or second counter electrodes, so that the first defibrillation waveform follows a first pathway;

determining if fibrillation was successfully terminated;

if fibrillation was not successfully terminated, automatically delivering a second defibrillation waveform using the coil electrode and any of the first or second counter electrodes, so that the second defibrillation waveform follows a second pathway through the heart tissue, wherein the second pathway is different from the first pathway; and if fibrillation was not successfully terminated by automatic delivery of the second defibrillation waveform, automatically selecting a third defibrillation waveform comprised concurrently of the first and second defibrillation waveforms that follow the first and second pathways, respectively; and repeating and automatically alternating delivery of the first defibrillation waveform, second defibrillation waveform, and third defibrillation waveform until defibrillation is confirmed or a maximum allowed number of waveforms to be delivered has been reached.

8. The method according to claim 7, wherein automatically and alternately delivering the first, second, and third defibrillation waveforms comprises selectively delivering the first, second, and third defibrillation waveforms in a predetermined sequence.

9. The method according to claim 7, wherein automatically and alternately delivering the first, second, and third defibrillation waveforms comprises selectively delivering the first, second, and third defibrillation waveforms until fibrillation is no longer detected between successive waveforms.

10. The method according to claim 7, wherein automatically selecting the third defibrillation waveform comprises delivering a defibrillation waveform using at least the coronary sinus counter electrode and the case counter electrode in a parallel combination, so that the third defibrillation waveform follows a dual pathway through the heart tissue.

11. A method of defibrillating a heart using a right ventricular coil electrode, a coronary sinus counter electrode, and a case counter electrode, the method comprising:

detecting a fibrillation;

delivering a first defibrillation waveform using a first electrode configuration comprising the right ventricular coil electrode and at least one of the coronary sinus counter electrode and the case counter electrode;

determining if fibrillation was successfully terminated; and if fibrillation was not successfully terminated, automatically delivering a second defibrillation waveform using a second electrode configuration comprising the right ventricular coil electrode and at least one of the coronary sinus counter electrode and the case counter electrode, wherein the second electrode configuration is different from the first electrode configuration;

if fibrillation was not successfully terminated by automatic delivery of the second defibrillation waveform, automatically selecting a third defibrillation waveform comprised concurrently of the first and second defibrillation waveforms that follow the first and second pathways, respectively; and repeating and automatically alternating delivery of the first defibrillation waveform, second defibrillation waveform, and third defibrillation waveform until defibrillation is confirmed or a maximum allowed number of waveforms to be delivered has been reached.

12. The method according to claim 11, wherein the first, second and third defibrillation waveforms comprises selectively delivering the first, second, and third defibrillation waveforms in a predetermined sequence.

13. The method according to claim 11, wherein delivering the first, second, and third defibrillation waveforms comprises selectively delivering the first, second, and third defibrillation waveforms until fibrillation is no longer detected between successive waveforms.

14. The method according to claim 11, wherein the first and second defibrillation waveforms comprise different types of waveforms.

15. A method of automatically alternating between at least a coronary sinus counter electrode and a case counter electrode, for use in a cardiac defibrillator, comprising:

detecting a fibrillation;

delivering a first defibrillation waveform using a first counter electrode, so that the first defibrillation waveform follows a first pathway through a cardiac tissue;

determining if fibrillation was successfully terminated;

if fibrillation was not successfully terminated, automatically selecting a previously designated preferred counter electrode to deliver a second defibrillation waveform, so that the second defibrillation waveform follows a second pathway through the cardiac tissue;

if fibrillation still was not successfully terminated, automatically selecting a third defibrillation waveform using a third counter electrode, so that the third defibrillation waveform follows a third pathway through the cardiac tissue, wherein the third pathway is different from the first pathway and from the second pathway; and repeating an alternating delivery of the first defibrillation waveform, second defibrillation waveform, and third defibrillation waveform until defibrillation is confirmed or the maximum allowed number of defibrillation waveforms to be delivered has been reached.

16. The method of claim 15, wherein the maximum allowed number of defibrillation waveforms to be delivered is at least six waveforms.

17. A cardiac defibrillator comprising:

means for detecting fibrillation;

means for delivering a first defibrillation waveform using a first electrode configuration;

means for determining if the fibrillation was successfully terminated; and means for delivering another defibrillation waveform using a second electrode configuration in response to determining that fibrillation was not terminated; and means for repeating an alternating delivery of the first defibrillation waveform and the another defibrillation waveform until defibrillation is confirmed or the maximum allowed number of waveforms to be delivered has been reached.

18. The cardiac defibrillator of claim 17, wherein the maximum allowed number of waveforms to be delivered is at least four waveforms.

19. A cardiac defibrillator capable of automatically alternating between at least a first counter electrode positioned adjacent a left cardiac chamber and a second remotely disposed counter electrode, comprising:

a sensor that detects fibrillation;

a pulse generator connected to the sensor, that delivers a first defibrillation waveform using a coil electrode positioned in a right chamber, and any of the first or second counter electrodes, so that the first defibrillation waveform follows a first pathway;

a detector, connected to the sensor, that determines if fibrillation was successfully terminated;

wherein if the detector determines that fibrillation was not successfully terminated, a control circuit automatically selects a second defibrillation waveform using the coil electrode and any of the first or second counter electrodes, so that the second defibrillation waveform follows a second pathway through the heart tissue;

wherein the second pathway is different from the first pathway; and wherein the pulse generator continues to automatically repeat and alternately deliver the first and second defibrillation waveforms, in response to unsuccessful termination of the fibrillation.

20. A cardiac defibrillator comprising:

fibrillation detection circuitry that is operative to detect fibrillation;

a stimulation generator that is operative to generate a defibrillation waveform for delivery to a patient's heart;

a plurality of electrodes comprising a right ventricular coil electrode, a coronary sinus counter electrode and a case counter electrode;

a detector that determines if fibrillation was successfully terminated; and a control circuit connected to the fibrillation detection circuitry, the stimulation generator, and the detector, wherein the control circuitry is responsive to detection of fibrillation to select a first electrode configuration for delivery of a first defibrillation waveform, and wherein the control circuitry is responsive to the detector determining that the fibrillation was not terminated to automatically select a second electrode configuration to deliver a second defibrillation waveform, wherein the second electrode configuration is different from the first electrode configuration;

wherein the control circuit is responsive to the detector determining that the fibrillation was not terminated by the delivery of the second defibrillation waveform to repeat an alternating delivery of the first defibrillation waveform and the second defibrillation waveform until defibrillation is confirmed or the maximum allowed number of waveforms to be delivered has been reached.

21. The cardiac defibrillator of claim 20, wherein the maximum allowed number of waveforms to be delivered is at least four waveforms.

22. A cardiac defibrillator comprising:

means for detecting fibrillation;

means for delivering a first defibrillation waveform using a first electrode configuration;

means for determining if the fibrillation was successfully terminated; and means for delivering a second defibrillation waveform using a second electrode configuration in response to determining that fibrillation was not terminated;

wherein, in response to a detected fibrillation, automatically selecting a third defibrillation waveform comprising concurrently the first and second defibrillation waveforms that follow the first and second pathways, respectively; and wherein repeating and automatically alternating delivery of the first defibrillation waveform, second defibrillation waveform, and third defibrillation waveform until defibrillation is confirmed or a maximum allowed number of waveforms to be delivered has been reached.

23. A cardiac defibrillator capable of automatically alternating between at least a first counter electrode positioned adjacent a left cardiac chamber and a second remotely disposed counter electrode, comprising:
   a sensor that detects fibrillation;
   a pulse generator connected to the sensor, that delivers a first defibrillation waveform using a coil electrode positioned in a right chamber, and any of the first or second counter electrodes, so that the first defibrillation waveform follows a first pathway; and
   a detector, connected to the sensor, that determines if fibrillation was successfully terminated;
   wherein if the detector determines that fibrillation was not successfully terminated, a control circuit automatically selects a second defibrillation waveform using the coil electrode and any of the first or second counter electrodes, so that the second defibrillation waveform follows a second pathway through the heart tissue;
   wherein the second pathway is different from the first pathway;
   wherein, in response to a detected fibrillation, the control circuit automatically selects a third defibrillation waveform comprised concurrently of the first and second defibrillation waveforms that follow the first and second pathways, respectively; and
   wherein the control circuit repeats and automatically alternates delivery of the first defibrillation waveform, second defibrillation waveform, and third defibrillation waveform until defibrillation is confirmed or a maximum allowed number of waveforms to be delivered has been reached.

24. A cardiac defibrillator comprising:
   fibrillation detection circuitry that is operative to detect fibrillation;
   a stimulation generator that is operative to generate a defibrillation waveform for delivery to a patient's heart;
   a plurality of electrodes comprising a right ventricular coil electrode, a coronary sinus counter electrode and a case counter electrode;
   a detector that determines if fibrillation was successfully terminated; and
   a control circuit connected to the fibrillation detection circuitry, the stimulation generator, and the detector, wherein the control circuitry is responsive to detection of fibrillation to select a first electrode configuration for delivery of a first defibrillation waveform, and wherein the control circuitry is responsive to the detector determining that the fibrillation was not terminated to automatically elect a second electrode configuration to deliver a second defibrillation waveform, wherein the second electrode configuration is different from the first electrode configuration;
   wherein, in response to a detected fibrillation, the control circuit automatically selects a third defibrillation waveform comprised concurrently of the first and second defibrillation waveforms that follow the first and second pathways, respectively; and
   wherein the control circuit repeats and automatically alternates delivery of the first defibrillation waveform, second defibrillation waveform, and third defibrillation waveform until defibrillation is confirmed or a maximum allowed number of waveforms to be delivered has been reached.

25. The cardiac defibrillator according to claim 24, wherein the first and second waveforms comprise different types of waveforms.

* * * * *